(12) United States Patent
Matheson et al.

(10) Patent No.: US 8,329,609 B2
(45) Date of Patent: *Dec. 11, 2012

(54) PROCESS FOR PREPARING ALKOXYLATION CATALYST AND ALKOXYLATION PROCESS

(75) Inventors: Kenneth Lee Matheson, Lake Charles, LA (US); Masikana Millan Mdleleni, Lake Charles, LA (US); Tad Curtis Hebdon, Lake Charles, LA (US); Herbert Olin Perkins, Orange, TX (US)

(73) Assignee: Sasol North America Inc., Houston, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/311,273

(22) Filed: Dec. 5, 2011

(65) Prior Publication Data

US 2012/0078001 A1    Mar. 29, 2012

Related U.S. Application Data

(63) Continuation of application No. 11/217,779, filed on Sep. 1, 2005.

(51) Int. Cl.
*B01J 21/00* (2006.01)
*B01J 23/00* (2006.01)
*B01J 25/00* (2006.01)
*B01J 29/00* (2006.01)
*B01J 31/00* (2006.01)

(52) U.S. Cl. ......... 502/150; 502/100; 502/171; 502/172

(58) Field of Classification Search ................... 502/150, 502/100, 171, 172

See application file for complete search history.

(56) References Cited

U.S. PATENT DOCUMENTS 5,627,121 A * 5/1997 Lin et al. ...................... 502/170

* cited by examiner

*Primary Examiner* — James McDonough
(74) *Attorney, Agent, or Firm* — Bushman & Associates, P.C.

(57) ABSTRACT

A process for preparing an alkoxylation catalyst wherein a catalyst precursor which is formed from an alkoxylated alcohol and an alkaline earth metal compound to form a dispersion of an alkaline earth metal species is reacted with propylene oxide to propoxylate at least a portion of the ethoxylated alcohol.

16 Claims, No Drawings

PROCESS FOR PREPARING ALKOXYLATION CATALYST AND ALKOXYLATION PROCESS

BACKGROUND OF THE INVENTION

1. Field of the Invention

The present invention relates to the preparation of an alkoxylation catalyst and to a process of alkoxylation using the thus prepared catalyst.

2. Description of Prior Art

Alkoxylated esters and compounds containing active hydrogen atoms such as alcohols, find utility in a wide variety of products, e.g., surfactants. Generally, an alkoxylation reaction involving a compound having an active hydrogen is conducted by the condensation of an alkylene oxide using a suitable catalyst. Because of the nature of the reaction, a mixture of product species is obtained having a rather wide range of molecular weights.

U.S. Pat. Nos. 4,775,653; 4,835,321; 4,754,075; 4,820,673; 5,220,077; and 5,627,121, all of which are incorporated herein by reference for all purposes, disclose the use of a calcium-based catalyst in the alkoxylation of various compounds such as alcohols and carboxylated compounds, e.g., esters.

SUMMARY OF THE INVENTION

According to a preferred aspect of the present invention, an alkoxylation catalyst of improved activity is produced. Additionally, catalysts prepared according to a preferred embodiment of the present invention exhibit greater stability vis-a-vis settling of slurried catalyst particles. Further, alkoxylation catalysts according to preferred embodiments of the present invention, block unwanted growth of ethoxylated alcohols in the catalyst which results in reduced formation of high molecular weight ethylene oxide adducts in the resulting products produced using the catalysts, and thereby reduces visual haze.

In accordance with a particularly preferred embodiment of the present invention, an alkoxylation catalyst is prepared by reacting a catalyst precursor comprising an ethoxylated alcohol and a dispersed alkaline earth metal compound, with propylene oxide under conditions to propoxylate at least a portion of the ethoxylated alcohol.

In another preferred aspect of the present invention there is provided a process for alkoxylating compounds having active hydrogen atoms, e.g., alcohols and carboxylated compound, e.g., esters, using a catalyst prepared in accordance with a preferred embodiment of the present invention.

DESCRIPTION OF THE PREFERRED EMBODIMENTS

The catalysts of the present invention are based on the unexpected finding that by subjecting certain prior art alkoxylation catalysts to propoxylation conditions, surprising results with respect to catalyst activity and stability as well as an improvement in the appearance of products produced using the catalyst, are achieved. The prior art catalysts which are treated according to the process of the present invention to produce the alkoxylation catalysts of the present invention are referred to herein as "catalyst precursors."

Preparation of Catalyst A

One of the catalyst precursors, referred to herein as Catalyst A, is disclosed in U.S. Pat. Nos. 4,775,653 ('653 patent) and 5,220,077 ('077 patent). As disclosed in the '653 and '077 patents, Catalyst A is prepared by admixing and reacting an ethoxylated alcohol mixture containing an ethoxylated alcohol having the general formula:

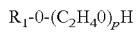

wherein $R_1$ is an organic radical containing from about 1 to about 30 carbon atoms and p is an integer of from 1-30, an alkaline earth metal-containing compound which is at least partially dispersible in the ethoxylated alcohol mixture, an inorganic acid, and a metal alkoxide selected from compounds having the formulas

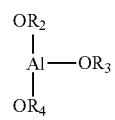

and

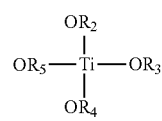

wherein $R_2$, $R_3$, $R_4$, and $R_5$ are each a hydrocarbon radical containing from about 1 to about 30, preferably from about 8 to about 14, carbon atoms. In the process of preparing Catalyst A, the alkaline earth metal compound and the ethoxylated alcohol mixture are mixed prior to addition of the metal alkoxide, the mixture being heated to a temperature and for a time sufficient to effect at least a partial exchange reaction between the alkoxide groups of the metal alkoxide and the hydroxyl groups of the ethoxylated alcohol.

The ethoxylated alcohols used can be prepared by methods well known in the art for preparing ethylene oxide adducts of alcohols. The ethoxylated alcohol mixture used in preparing Catalyst A typically contains free alcohol, the amount and type of which will vary depending upon the source of the ethoxylated alcohol. Generally speaking, the ethoxylated alcohol mixture will contain from about 1% to about 60% by weight free alcohol.

The alkaline earth metal compound used is one which is at least partially dispersible in the ethoxylated alcohol. As used herein, the term "dispersible" refers to a compound which solubilizes or otherwise interacts with the ethoxylated alcohol in such a manner that it becomes a new species of alkaline earth metal compound. It is to be understood, however, that inasmuch as the mechanism is not completely understood, the term "dispersible" or "soluble" is not intended to be limited to the formation of a truly dissolved alkaline earth metal species as would be commonly understood in the case of ordinary solubilization. While compounds such as calcium and strontium hydride, calcium and strontium acetate, calcium and strontium oxalate, etc. may be used, it is preferred that the alkaline earth metal compound be calcium or strontium oxide, calcium or strontium hydroxide, calcium or strontium hydride or a mixture thereof.

The inorganic acids useful include the acids themselves as well as "acid salts". Thus, non-limiting examples of inorganic acids include sulphuric acid, hydrochloric acid, hydrofluoric acid, phosphoric acid, pyrophosphoric acid, ammonium biflouride, ammonium sulfate, etc. Particularly preferred are the oxy acids, such as sulphuric acid.

In preparing Catalyst A relative amounts of the various components can vary widely. For example, the mol ratio of the alkaline earth metal compound to the metal alkoxide can vary from about 1:1 to about 10:1, based on alkaline earth metal compound and metal of the alkoxide, respectively. The mol ratio of the inorganic acid to the metal alkoxide can vary from about 0.25:1 to about 4:1, based on the ratio of the acid equivalent e.g. acid hydrogens, in the inorganic acid to the metal of the alkoxide, respectively. It is generally preferred that the combined concentration of the alkaline earth metal compound, the inorganic acid and the metal alkoxide be present in an amount of from about 1 to about 10% by weight, the ethoxylated alcohol and diluents such as free alcohol being present in an amount of from about 90-99% by weight. As noted, depending on the source and type of the ethoxylated alcohol, free alcohol content can range from about 1% by weight to about 60% by weight.

Generally speaking, the order of addition of the various components of Catalyst A is immaterial with the exception that the alkaline earth metal compound must be added prior to addition of the metal alkoxide. Thus, although it is common practice to admix the ethoxylated alcohol, the alkaline earth metal compound and the inorganic acid, followed by the addition of the metal alkoxide, the process can also be carried out by reversing the order of addition of the metal alkoxide and the inorganic acid.

In addition to the above components Catalyst A can contain, with advantage, organic acids. Suitable organic acids are those carboxylic acids which have greater miscibility in hydrocarbon solvents than in water. Such carboxylic acids, which may generally be considered fatty acids, have a carbon chain length versus acid functionality which provides their greater miscibility or solubility in hydrocarbons. Non-limiting examples of fatty acids include those natural or synthetic mono-functional carboxylic acids wherein the carbon chain length is greater than about 5 carbon atoms, generally from about 5 to about 15 carbon atoms. Specific examples of such suitable acids include hexanoic, octanoic, nonanoic, 2-ethyl hexanoic, neodecanoic, isooctanoic, stearic, napthanoic, and mixtures or isomers of such acids. While it is preferred that the acids, if used, be saturated, they may optionally contain other functional groups such as hydroxyl groups, amine groups, etc. which do not interfere with the process. It has been found that the use of the fatty acids leads to a better dispersion of the alkaline earth metal compound and that the active catalyst suspension is more stable in terms of the solids remaining dispersed.

In preparing Catalyst A, a typical ethoxylated alcohol is admixed with a suitable alkaline earth metal containing compound such as calcium oxide and the mixture stirred for a suitable period of time until at least some of the calcium compound disperses or solubilizes in the ethoxylated alcohol. Generally, this is accomplished by stirring, or other means of agitation to achieve intimate and thorough contact, at a temperature of generally from about 25° C. to about 150° C. (usually below the boiling point of the ethoxylated alcohol) for a sufficient period of time. The dispersion time can vary from about 0.5 hours to about 20 hours. Longer times can be used if desired. Once the dispersion has been formed, as evidenced, e.g., by the presence of titratable alkalinity, the inorganic acid is then slowly or incrementally added. The metal, e.g., aluminum alkoxide is then added and stirring of the mixture continued and the mixture heated to a temperature and for a sufficient period of time to effect at least a partial exchange reaction between the alkoxide groups of the metal alkoxide and the hydroxyl group of the ethoxylated alcohol.

The precise temperature to which Catalyst A is heated will, of course, depend upon the nature of the components employed. However, as noted above, the heating is usually carried out at a temperature and for a period of time sufficient to effect at least a partial exchange reaction between the alkoxide groups of the metal alkoxide and the hydroxyl group of the ethoxylated alcohol. This point can generally be determined by the evolution of alcohol which distills out of the mixture. It is preferred that the heating be carried on until the mixture has reached a substantially constant boiling point. The desired activation temperature should, for a given pressure, approximate the boiling point of a substantial fraction of the free alcohols derived from the $R_2$, $R_3$ and $R_4$ group of the metal alkoxide. At this point, maximum exchange has likely occurred between the alkoxide groups of the metal alkoxide and the hydroxyl group of the ethoxylated alcohol. It will be recognized that when the metal alkoxide utilized is one where $R_2$, $R_3$, $R_4$ and $R_5$ are long chain, e.g. 10 to 14 carbon atoms and longer, the alcohols produced in the exchange reaction are high boiling. Accordingly, very little if any distillation of alcohol occurs without the application of extremely high temperatures which can cause unwanted side reactions. In such cases, the heating can be carried out to a temperature of about 190°-300° C. and more preferably from about 230°-260° C. Lower temperatures may be employed when the process is conducted under reduced pressure, e.g. at a pressure of about 150-300 Torr, temperature in the range of about 160° C. to about 210° C. are suitable. The desired temperature range can be determined by sampling the dispersion as it is being heated at various times during the heating cycle and subjecting the samples to an ethoxylation reaction. When the desired degree of activity is achieved in the ethoxylation reaction, heating can be discontinued. Generally, however, the time of heating can vary from about 0.1 hour to about 5 hours, generally in the range of from about 0.2 hour to about 1 hour.

Preparation of Catalyst B

As detailed in U.S. Pat. No. 5,627,121, another catalyst precursor referred to herein as Catalyst B is formed by reacting an ethoxylated alcohol mixture, a alkaline earth metal compound that is at least partially dispersible in the ethoxylated alcohol mixture and a carboxylic acid. The ethoxylated alcohols useful in forming Catalyst B are the same as those defined by Formula 1.

The ethoxylated alcohol mixture used can be prepared by methods well known in the art for preparing alkylene oxide adducts of alcohols. Alternately, the alkylene oxide adducts can be prepared according to the process of the present invention. The ethoxylated alcohol mixture used in preparing Catalyst B typically contains free alcohol, the amount and type of which will vary depending upon the source of the ethoxylated alcohol. Generally speaking, the ethoxylated alcohol mixture will contain from about 1% to about 60% by weight free alcohol.

The alkaline earth metal compounds used in preparing Catalyst B are as described above with respect to Catalyst A.

The carboxylic acids used in preparing Catalyst B are as described above with respect to Catalyst A.

The inorganic acids that are useful in preparing Catalyst B are those as described above with respect to Catalyst A.

The relative amounts of the various components can vary widely, and in general, are defined above with respect to Catalyst A.

In forming Catalyst B, the ethoxylated alcohol mixture, the alkaline earth metal compound, the carboxylic acid, and the neutralizing acid are reacted or combined under conditions that prevent any significant loss of water that is either initially present or formed during the reaction. Preventing loss of water is typically accomplished by conducting the reaction at a low enough temperature, e.g., room temperature, to prevent loss of water. Alternately, if the reaction is conducted at elevated temperatures, super-atmospheric pressure can be used to prevent loss of water. Preferably, the reaction is conducted at elevated temperatures under reflux to prevent loss of water.

In a preferred method of forming Catalyst B, the alkaline earth metal compound, e.g., calcium hydroxide, and the ethoxylated alcohol mixture are charged into a suitable stirred vessel equipped with a reflux condenser, following which the carboxylic acid is added. Generally, the three components are mixed at room temperature, although higher temperatures can be used. This reaction mixture is then heated generally to a temperature of from about 30° to 45° C. for a period of time sufficient to solubilize the calcium-containing compound. Generally speaking, the reaction mixture is reacted for a period of from about 0.5 to about 2 hours. Following solubilization of the calcium compound, a mineral acid, e.g., sulfuric acid, is introduced into the reaction mixture in an amount sufficient to neutralize at least 25% of the titratable alkalinity present in the reaction mixture. The reaction mixture can optionally be sparged with an inert gas such as nitrogen.

As noted above, to prepare the catalysts of the present invention, a suitable catalyst precursor, e.g., Catalyst A or Catalyst B, described above, is reacted with propylene oxide under propoxylation conditions to effect at least propoxylation of at least a portion of the ethoxylated alcohols present in the catalyst precursor. The formula of ethoxylated alcohols present in either of the catalyst precursors is given by Formula I above. Following propoxylation according to the process of the present invention, there is produced an ethoxylated/propoxylated alcohol having the formula $$R_1\text{-}O\text{-}(C_2H_4O)_p\text{-}(C_3H_6O)_tH \qquad IV$$

wherein t is from 1 to 15, preferably from 1 to 10, more preferably from 1 to 7. Particularly preferred ethoxylated/propoxylated species coming within Formula IV which are useful in the present invention are those wherein $R_1$ contains from 8 to 14 carbon atoms, p is from 2 to 6 and t is from 1 to 3, most preferably from 1 to 1.5. It will be understood that, as in the case of all alkoxylated species of alcohols, there is a distribution of the alkoxy groups, the numbers above referring to the average number of ethoxy/propoxy groups present in the alkoxylated species.

In general the catalysts of the present invention are prepared by reacting one of the catalyst precursors with the desired amount of propylene oxide in a standard alkoxylation reactor. Generally the propoxylation reaction is conducted at a temperature from 95 to 200° C. and from 15 to 75 psig propylene oxide pressure.

To more illustrate the present invention, the following non-limiting examples are presented. In the following example, the following procedure was employed to prepare the catalyst, e.g., Catalyst A or Catalyst B:

EXAMPLE 1

85 gram portions of catalyst precursors were separately subjected to propylene oxide addition in the standard alkoxylation reactor at a temperature of 120 to 150° C. and a pressure of 40 to 50 psig propylene oxide (PPO) so as to result in the addition of 1.0 to 1.5 mols of propylene oxide. The thus prepared catalysts were compared with Catalyst A and Catalyst B, i.e., the catalyst precursor, to determine activity. The catalyst samples were tested for activity on the basis of time to effect addition of a given amount of ethylene oxide to an ALFOL® 12 alcohol, a alcohol marketed by Sasol North America, Inc. In all cases, the amount of catalyst employed was 0.1 wt. %.

Table 1 below shows the results using the various catalyst in preparing an ethoxylated $C_{12}$ alcohol containing 7 mols of ethylene oxide. In Table 1, in all cases, the catalysts according to the present invention contained 1 mol of propylene oxide as indicated by Catalyst A+1 PPO, Catalyst B+1 PPO, etc.

TABLE 1

| Catalyst | Run Time (Min) |
|---|---|
| Catalyst A | 38 |
| Catalyst A + 1 PPO | 32 |
| Catayst B | 56 |
| Catalyst B + 1 PPO | 43 |

Table 2 below shows results for the addition of two mols of ethylene oxide to the $C_{12}$ alcohol.

TABLE 2

| Catalyst | Run Time (Min) |
|---|---|
| Catalyst B | 43 |
| Catalyst B + 1.5 PPO | 34 |

As can be seen from the data in Table 1 and Table 2, the addition of propylene oxide to either Catalyst A or Catalyst B results in improved activity of the respective catalyst.

EXAMPLE 2

This Example demonstrates the effect of adding different levels of propylene oxide to the catalyst precursors in terms of catalyst stability, i.e., the ability of the catalyst to remain as a generally homogeneous dispersion over a period of time. The procedure of Example 1 was followed with respect to the propoxylation of Catalyst B. Samples of propoxylated Catalyst B containing 0.5, 1.0 and 1.5 mols of PPO, respectively, were prepared and compared with unpropoxylated Catalyst B. In general, after periods of 1 week, 2 weeks, and 3.5 weeks, all of the propoxylated samples exhibited greater stability, i.e., remained better dispersed than the non-propoxylated Catalyst B. This dispersion improvement was not noticed with respect to similarly propoxylated samples of Catalyst A.

EXAMPLE 3

The procedure of Example 1 was followed with respect to determining the effect of propoxylation of the catalyst precursors vis-a-vis ethoxylation activity with the exception that the alcohol employed was Safol™ 23, an essentially linear C12-13 binary alcohol marketed by Sasol North America, Inc. In all cases, 7 mols of ethylene oxide were added to the alcohol. The results comparing Catalyst B and a catalyst according to the present invention are shown in Table 3 below.

TABLE 3

| Catalyst | Run Time (Min) |
|---|---|
| Catalyst B | 55 |
| Catalyst B + 0.5 PPO | 49 |
| Catayst B + 1.0 PPO | 55 |
| Catalyst B + 1.5 PPO | 77 |

Table 4 below shows results using propoxylated Catalyst A:

TABLE 4

| Catalyst | Run Time (Min) |
|---|---|
| Catalyst A | 48 |
| Catalyst A + 0.5 PPO | 58 |
| Catayst A + 1.0 PPO | 43 |
| Catalyst A + 1.5 PPO | 40 |

As can be seen from Tables 3 and 4 in the case of the propoxylated Catalyst B (Table 3) at low levels of propoxylation (0.5 mols) the activity of the catalyst was enhanced. However, as the amount of propylene oxide addition increased, catalyst activity decreases as compared to the unmodified (unpropoxylated) catalyst precursor.

With respect to Table 4, it can be seen that increasing amounts of propoxylation increase the activity of the propoxylated modified Catalyst A, amounts of propylene oxide addition of greater than about 1 mol rendering the resulting catalyst more active.

EXAMPLE 3

The procedure of Example 1 was followed in terms of preparing 7 mol ethoxylates of the Safol™ 23 alcohol. Both in the case of propoxylated Catalyst A and B, it was found that from 1.0 to 1.5 mols of propylene oxide added resulted in less residual catalyst haze. It was also noted with respect to Catalyst A propoxylated at the 0.5 mol level that there appeared to be an increase in haze of the ethoxylated product.

As can be seen from the above results, the process of the present invention provides alkoxylation catalysts that, as compared to prior art alkoxylation catalysts, exhibit greater activity, are more stable, and produce a product with less haze. As the data above demonstrates, depending upon the catalyst precursor and the desired results, e.g., catalyst activity versus haze in the end product, the amount of propylene oxide added to the catalyst precursor is tailored.

Modifications of the compositions, procedures and conditions disclosed herein that will still embody the concept of the improvements described should readily suggest themselves to those skilled in the art, and are intended to be encompassed within the spirit of the invention presently disclosed herein as well as the scope of the appended claims.

What is claimed is:

1. An alkoxylation process comprising:
reacting (I) a catalyst precursor selected from the group consisting of:
(1) Catalyst A formed by reacting a reaction medium comprising an ethoxylated alcohol mixture comprising compounds having the general formula:

$$R_1\text{-O-}(C_2H_4O)_pH \qquad \text{I}$$

wherein $R_1$ is an organic radical containing from 1 to 30 carbon atoms, and p is an integer of from 1 to 30, an alkaline earth metal compound selected from the group consisting of calcium-containing compounds, strontium-containing compounds and mixtures thereof which is at least partially dispersible in said ethoxylated alcohol mixture, an inorganic acid, and a metal alkoxide of a Lewis acidic metal, said reaction medium being optionally heated to a temperature and for a time sufficient to effect at least a partial exchange reaction between the alkoxide groups of said metal alkoxide, and the hydroxyl groups of said ethoxylated alcohol; and
(2) Catalyst B formed by reacting an ethoxylated alcohol mixture comprising compounds having the Formula I, an alkaline earth metal compound selected from the group consisting of calcium-containing compounds, strontium-containing compounds and mixtures thereof which is at least partially dispersible in said ethoxylated alcohol mixture, and a carboxylic acid having from 4 to 15 carbon atoms, the mol ratio of alkaline earth metal compound to said carboxylic acid being from about 15:1 to 1:1, to produce an alkaline earth metal containing composition having titratable alkalinity, said alkaline earth metal containing composition being obtained under conditions to prevent loss of water, and adding an amount of an inorganic acid to neutralize at least 25% of said titratable alkalinity under conditions to prevent loss of water to produce a partially neutralized compound;
with (II) propylene oxide under conditions to propoxylate Catalyst A or Catalyst B to produce a propoxylated Catalyst A or a propoxylated Catalyst B, respectively; and
(3) reacting, in the presence of one of said propoxylated Catalyst A or propoxylated Catalyst B, a reactant selected from the group consisting of compounds having active hydrogen atoms, carboxylated compounds and mixtures thereof, with ethylene oxide under alkoxylation conditions to produce an alkoxylated derivative of said reactant.

2. The process of claim 1, wherein $R_1$ is from 8 to 14 and p is from 2 to 10 and there are from 0.5 to 1.5 moles of added propylene oxide.

3. The process of claim 1, wherein said calcium-containing compound is selected from the group consisting of calcium oxide, calcium hydroxide, calcium hydride and mixtures thereof.

4. The process of claim 1, wherein said strontium-containing compound is selected from the group consisting of strontium oxide, strontium hydroxide, strontium hydride and mixtures thereof.

5. The process of claim 1, wherein said metal alkoxide is selected from compounds having the formulas:

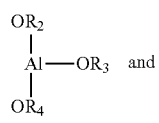

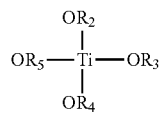

and mixtures thereof wherein $R_2$ $R_3$ $R_4$ and $R_5$ is each a hydrocarbon radical containing from about 1 to about 30 carbon atoms.

6. The process of claim 5, wherein $R_2$ $R_3$ $R_4$ and $R_5$ contains from about 8 to about 14 carbon atoms.

7. The process of claim 1, wherein said reaction between said catalyst precursor and said propylene oxide is conducted at a temperature of from 95 to 200° C.

8. The process of claim 1, wherein said inorganic acid is sulphuric acid.

9. The process of claim 1, wherein the mol ratio of said alkaline earth metal compound to said metal alkoxide is from about 0.25:1 to about 4:1, calculated as acidic hydrogen and aluminum, respectively.

10. The process of claim 1, including adding to said reaction medium a carboxylic acid having from 4 to 15 carbon atoms.

11. The process of claim 1, including removing water from said reaction medium prior to addition of said metal alkoxide.

12. The process of claim 1, including heating the partially neutralized composition at a temperature of from about 90° to about 130° C. under reflux conditions.

13. The process of claim 12, wherein said heating is conducted for a period of 1 to 5 hours.

14. The process of claim 1, wherein said inorganic acid is selected from the group consisting of sulphuric acid, phosphoric acid, hydrochloric acid and mixtures thereof.

15. The process of claim 1, wherein said compound having an active hydrogen atom is an alcohol.

16. The process of claim 1, wherein said carboxylated compound is an ester.

* * * * *

UNITED STATES PATENT AND TRADEMARK OFFICE Certificate

Patent No. 8,329,609 B2                                                   Patented: December 11, 2012

On petition requesting issuance of a certificate for correction of inventorship pursuant to 35 U.S.C. 256, it has been found that the above identified patent, through error and without any deceptive intent, improperly sets forth the inventorship.

Accordingly, it is hereby certified that the correct inventorship of this patent is: Kenneth Lee Matheson, Lake Charles, LA (US); Masikana Millan Mdleleni, Lake Charles, LA (US); Tad Curtis Hebdon, Lake Charles, LA (US); Herbert Olin Perkins, Orange, TX (US); and Melanie Anne Sharp, Westlake, LA (US).

Signed and Sealed this Twenty-first Day of May 2013.

<div style="text-align: right;">
EMILY M. LE<br>
<em>Supervisory Patent Examiner</em><br>
Art Unit 1734<br>
Technology Center 1700
</div>